United States Patent [19]

Takeuchi et al.

[11] Patent Number: 5,338,720
[45] Date of Patent: Aug. 16, 1994

[54] TRIAZOLE COMPOUNDS AND HERBICIDAL COMPOSITIONS

[75] Inventors: Masaki Takeuchi, Saitama; Mitsuru Kanzaki, Shizuoka, both of Japan

[73] Assignee: Chugai Seiyaku Kabushiki Kaisha, Tokyo, Japan

[21] Appl. No.: 972,461

[22] PCT Filed: Aug. 3, 1991

[86] PCT No.: PCT/JP91/01041

§ 371 Date: Feb. 3, 1993

§ 102(e) Date: Feb. 3, 1993

[87] PCT Pub. No.: WO92/02512

PCT Pub. Date: Feb. 20, 1992

[30] Foreign Application Priority Data

Aug. 3, 1990 [JP] Japan .................................. 2-206483

[51] Int. Cl.$^5$ .................. A01N 43/653; C07D 249/12
[52] U.S. Cl. ..................................... 504/273; 548/264.2
[58] Field of Search ....................... 504/273; 548/264.2

[56] References Cited

U.S. PATENT DOCUMENTS

| | | | |
|---|---|---|---|
| 3,308,131 | 3/1967 | McKusick | 260/294 |
| 3,816,392 | 6/1974 | Weaver | 260/157 |
| 3,897,440 | 7/1975 | Beck et al. | 260/294.86 |
| 3,952,001 | 4/1976 | Brookes | 260/308 R |
| 4,005,202 | 1/1977 | Beard | 424/278 |
| 4,280,831 | 7/1981 | Patel | 71/92 |

FOREIGN PATENT DOCUMENTS

| | | |
|---|---|---|
| 59-29880 | 3/1984 | Japan . |
| 100561 | 6/1985 | Japan . |
| 1106883 | 4/1989 | Japan . |
| 1121279 | 5/1989 | Japan . |
| 11481 | 1/1990 | Japan . |
| 390069A2 | 4/1991 | Japan . |
| 3279368 | 12/1991 | Japan .................. 548/264.2 |
| 1123947 | 8/1968 | United Kingdom . |
| 1157256 | 7/1969 | United Kingdom . |

OTHER PUBLICATIONS

U. Yoshihiro et al. "Carbamoyltriazole Derivative and Herbicide containing the derivative as active component", Patent Abstracts of Japan, Oct. 12, 1991, for JP 3279368.

U. Yoshihiro et al. "Preparation of carbamoyltriazole derivatives as herbicides", Chemical Abstracts, vol. 1992, p. 883.

*Primary Examiner*—Patricia L. Morris
*Attorney, Agent, or Firm*—Browdy and Neimark

[57] ABSTRACT

A triazole compound represented by the formula:

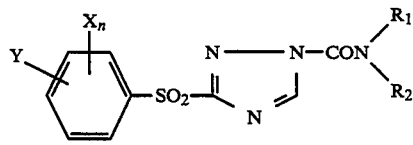

wherein X denotes a hydrogen atom, a halogen or a lower alkyl group, Y denotes a halogen substituted lower alkoxy group, $R_1$ and $R_2$ which may be the same or different each denotes an ethyl or propyl group, and n is an integer of 0–4, and a herbicidal composition comprising the compound as an active ingredient. The above compounds have excellent properties in that they not only exhibit marked herbicidal activities in a low dose against various weeds of rice paddies and plowed fields but also cause no injury to crops.

6 Claims, No Drawings

TRIAZOLE COMPOUNDS AND HERBICIDAL COMPOSITIONS

TECHNICAL FIELD

The present invention relates to triazole compounds represented by formula (I):

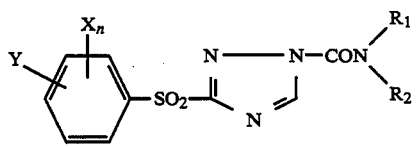

wherein X denotes a hydrogen atom, a halogen or a lower alkyl group, Y denotes a halogen substituted lower alkoxy, $R_1$ and $R_2$ which may be the same or different each denotes an ethyl or propyl group; and n is an integer of 0–4. The compounds have excellent properties in that they not only exhibit marked herbicidal activities in a low dose but also cause no injury to crops.

BACKGROUND ART

It is known that some triazole compounds exhibit herbicidal activities (see U.S. Pat. No. 4,280,831, Japanese Laid-open Patent Publication Nos. 59-39880, 60-100561, 61-178980, 63-14776, 1-121279 and 2-1481).

However, the conventional triazole herbicides harm crops or are unable to exhibit satisfactory herbicidal activities unless used in large amounts. A need has, therefore, existed for the development of triazole compounds that are free from these problems.

The present inventors directed their attention to the compounds disclosed in Japanese Laid-open Patent Publication Nos. 1-121279 and 2-1481. They conducted intensive studies in order to develop herbicides that exhibit excellent herbicidal activities in a lower dose than these compounds and furthermore do not cause any injury to crops. As a result, they found that excellent herbicides could be obtained only by replacing a substituent(s) contained in the phenyl group of the compounds mentioned in Japanese Laid-open Patent Publication Nos.1-121279 and 2-1481, by the other substituents. The present invention has been accomplished on the basis of this finding.

DISCLOSURE OF INVENTION

Production of the compounds of the present invention represented by formula I will typically proceed as follows. A starting material, namely, a compound represented by formula II:

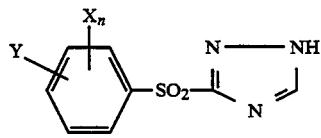

(wherein X, Y and n have the same meanings as defined above) is reacted with a compound of formula III:

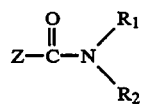

wherein $R_1$ and $R_2$ have the same meanings as defined above and Z denotes a halogen.

In this reaction, a compound of formula II is reacted with 1–2 equivalents, preferably 1–1.2 equivalents, of a compound of formula III in a suitable solvent in the presence of at least 1 equivalent, preferably 1–2 equivalents, of a deprotonating agent. The reaction temperature is in the range of 0°–100° C., preferably 20°–70° C. Suitable deprotonating agents include inorganic bases such as sodium hydroxide, potassium hydroxide, sodium carbonate, sodium bicarbonate and sodium hydride, and organic bases such as triethylamine and pyridine. Suitable solvents include hydrocarbons such as benzene, toluene and xylene; halogenated hydrocarbons such as methylene chloride and chloroform; ethers such as diethyl ether, tetrahydrofuran and dioxane; ketones such as acetone and methyl ethyl ketone; and others such as ethyl acetate, acetonitrile, dimethylformamide, pyridine, dimethyl sulfoxide, water, etc. These solvents may be used either on their own or as admixtures.

The starting compounds of formula II are novel per se and are included within the scope of the present invention. They can be prepared by dissolving a compound of formula IV:

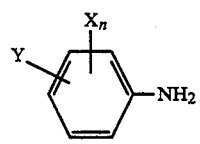

(wherein X, Y and n have the same meaning as defined above) in concentrated hydrochloric acid followed by addition of $NaNO_2$ to give a diazonium salt solution and adding to the solution a compound of formula V:

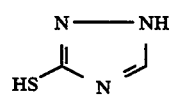

followed by oxidation. Any solvent that is inert to the reactants may be used in preparing the novel compounds of Formula II, and those already described in connection with the preparation of compounds of formula I, including dimethylformamide, may be employed.

The reaction temperature should be in the range of 0°–100° C., preferably 0°–70° C. The oxidation step may be performed in a suitable solvent using an oxidizing agent. Useful oxidizing agents include inorganic oxidizing agents such as hydrogen peroxide, potassium permanganate and chromic acid, and organic oxidizing agents such as peracetic acid and m-chloroperbenzoic acid. Solvents that can be used include methylene chloride, chloroform, acetone, acetic acid, water, etc., which may be used either alone or in admixture.

BEST MODE FOR CARRYING OUT THE INVENTION

The present invention is described hereinafter in greater detail with reference to examples. However, it should be appreciated that tile invention is not restricted to these examples. EXAMPLE 1

Synthesis of 3-[2-(2,2,2-trifluoroethoxy) phenylthio]-1, 2, 4-triazole

A 200-ml round-bottom flask is charged with conc. HCl (4 ml) and water (40 ml), and 2-(2,2,2trifluoroethoxy)aniline (3.82 g) is added. The resulting solution is cooled at a temperature of not more than 5° C. and an aqueous solution consisting of sodium nitrite (1.7 g) dissolved in water (10 ml) is added dropwise with tile temperature held at 4° C. or below, followed by stirring For one hour. In a separate step, 3-mercapto-1,2,4-triazole (4.5 g) and potassium hydroxide (2.2 g) is dissolved in water (40 ml) to give an aqueous solution which is cooled at 0° C. A preliminarily prepared diazonium salt solution is added dropwise to this aqueous solution. Thereafter, the resulting mixture is stirred at room temperature for about one hour. The organic layer is extracted with ethyl acetate, washed with water and dried. The solvent is distilled off and the resulting crude crystal is recrystallized with a mixed solvent of n-hexane and ethyl acetate; yield 4.4 g (71%); m.p. 100°–101° C.

Elemental analysis for $C_{10}H_8F_3N_3OS$ (MW, 275.253) Cal'd (%): C 43.64, H 2.93, N 15.27 Found (%): C 43.51, H 2.85, N 15.31

EXAMPLE 2

Synthesis of 1-(diethylcarbamoyl)-3-[2-(2,2,2-trifluoroethoxy)-phenylsulfonyl]-1,2,4-triazole (compound No.1)

3-[2-(2,2,2-trifluoroethoxy) phenylthio]-1,2,4-triazole (2.7 g) and diethyl carbamoyl chloride (1.4 g) are dissolved in acetone (40 ml) and potassium carbonate (1.4 g) is added, followed by reaction for 2 hours under reflux with stirring. Thereafter, the solvent is distilled off from the reaction mixture, and water and ethyl acetate are added to the resulting mixture. The organic layer is dried and concentrated. The resultant concentrate is dissolved in chloroform (50 ml) to give a solution. With the temperature held at 10° C. or below, m-chloroperbenzoic acid (3.4 g) is added to the solution. Thereafter, the resulting mixture is stirred at room temperature for 2 hours and washed with an aqueous solution of sodium bicarbonate. The chloroform layer is dried and distilled off to give a crude crystal. Recrystallization From a mixed solvent of n-hexane and ethyl acetate produces the end product; yield 3.1 g (75%); m.p. 134°–135° C.

Elemental analysis for $C_{15}H_{17}F_3N_4O_4S$ (MW, 406.385) Cal'd (%): C 44.33, H 4.22, N 13.79 Found (%): C 44.51, H 14.18, N 13.65

The compounds of formula I listed in Table 1 below can be synthesized by similar procedures.

TABLE 1

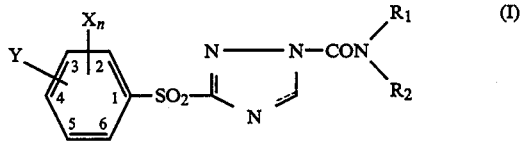

| Compound No. | $X_n$ | Y | $R_1$ | $R_2$ | Physical data |
|---|---|---|---|---|---|
| 1 | H | 2-OCH$_2$CF$_3$ | C$_2$H$_5$ | C$_2$H$_5$ | m.p. 134–135° C. |
| 2 | 6-CH$_3$ | 2-OCH$_2$CF$_3$ | C$_2$H$_5$ | C$_2$H$_5$ | m.p. 148–149° C. |
| 3 | H | 2-OCHF$_2$ | C$_2$H$_5$ | C$_2$H$_5$ | Oil NMR[1] |
| 4 | 6-CH$_3$ | 2-OCHF$_2$ | C$_2$H$_5$ | C$_2$H$_5$ | m.p. 82–83° C. |
| 5 | H | 2-OCF$_3$ | C$_2$H$_5$ | C$_2$H$_5$ | Oil NMR[2] |
| 6 | 6-Cl | 2-OCH$_2$CF$_3$ | C$_2$H$_5$ | C$_2$H$_5$ | m.p. 143–145° C. |
| 7 | H | 2-OCH$_2$CF$_3$ | C$_2$H$_5$ | n-C$_3$H$_7$ | m.p. 87–88° C. |

TABLE 1-continued

| Compound No. | $X_n$ | Y | $R_1$ | $R_2$ | Physical data |
|---|---|---|---|---|---|
| 8 | H | 2-OCH$_2$CF$_2$CHF$_2$ | C$_2$H$_5$ | C$_2$H$_5$ | m.p. 98–99° C. |
| 9 | 6-Cl | 2-OCH$_2$CF$_3$ | C$_2$H$_5$ | n-C$_3$H$_7$ | Oil NMR[3] |

[1] NMR: 1.28(6H, t), 3.60(4H, q), 6.01(1H, d), 7.30–8.39(4H, m), 8.82(1H, s)
[2] NMR: 1.26(6H, t), 3.58(4H, q), 7.32–8.40(4H, m), 8.86(1H, s)
[3] NMR: 0.76–1.88(8H, m), 3.35–3.77(4H, m), 4.38(2H, q), 6.92–7.69(3H, m), 8.83(1H, s)

Compounds of the present invention can be used to weed rice paddies, plowed fields, orchards and non-cultivated land. They can be applied at any time such as prior to sowing the seeds of crops, simultaneously with sowing, at the time of transplantation, at the seeding stage, or the subsequent growth stage. A suitable method of use can be selected from among various types of treatment including water surface treatment, soil treatment and foliage treatment.

In order to ensure maximum convenience in handling, compounds of the present invention may be mixed with various solid or liquid vehicles for common agrochemical formulations to prepare various formulations including wettable powders, emulsifiable concentrates, oil sprays, dusts, granules and flowables. If desired, various adjuvants may be added to tile drugs, such as dispersants, diluents, emulsifiers, spreaders, wetting agents, adsorbents, thickeners, antifoams and antifreezes.

The vehicles to be used may be either solid or liquid or combinations thereof. Illustrative vehicles include talc, clay, bentonite, kaolin, diatomaceous earth, calcium carbonate, kerosene, naphtha, xylene, cyclohexane, methylnaphthalene, benzene, acetone, dimethylformamide, glycol ether and N-methylpyrrolidone.

Illustrative adjuvants include polyoxyethylene alkylphenyl ether, polyoxyethylene sorbitan monooleate, ethylene oxide-propylene oxide copolymer, lignin sulfonates, sorbitan esters, soaps, sulfated oils, alkyl sulfate ester salts, petroleum sulfonates, dioctyl sulfosuccinate salts, alkyl benzene sulfonates, asphaltic amine salts, quaternary ammonium salts, alkyl pyridinium salts, alkyldimethyl betaine, alkylaminoethyl glycine, polyglycol sulfate esters, alkylaminesulfonic acids, isopropyl phosphate, carboxymethyl cellulose, polyvinyl alcohol, hydroxypropyl cellulose, ethylene glycol and xanthan gum.

Compounds of the present invention can be formulated in amounts freely selected from the range of 0.05-95 wt %. Preferred formulations contain such compounds in amounts of 1–70 wt %, vehicles in amounts of 1–99 wt % (preferably 40–90 wt %), and adjuvants in amounts of 0–20 wt% (preferably 1–7 wt%). Broader activity spectra may be expected if these compounds are used in admixture with other agrochemicals including bactericides, herbicides, growth control regulators, insecticides and acaricides, or with fertilizers.

It will be apparent to those having ordinary skill in the art that in the actual use of compounds of the present invention or admixtures thereof with compounds in the group of known herbicides, the amount in which they are used should be appropriately selected in accordance with various factors such as the season they are used, the weather conditions, method of use, dosage form, place of use, the target weeds and the crop to be treated. As guide figures, 0.5-50 g, preferably 1-20 g, per are of the compound of the present invention may be used.

The following test examples are given for the purpose of demonstrating the effectiveness of compounds of the present invention as herbicides.

Test Example 1

Wagner pots (1/5,000 are) were filled with soil from a plowed field. After sowing wheat and soybean seeds, they were covered with soil from a plowed field containing weed seeds. The soil covering had a thickness of 2 cm. Immediately thereafter, emulsifiable concentrates formulated by the method described in Formulation Example 3 (see below) were weighed, diluted in 5 ml of water per pot and applied over the soil surface. Control and growth were conducted in a greenhouse and the herbicidal activities and extent of crop injury were investigated four weeks after the treatment. The results are summarized in Table 2.

The dose which exhibits score 4.5 (90% herbicidal activity) is determined for each of the test compounds by the graph made on the basis of the data in Table 2. The values thus determined are shown in Table 3.

In Table 2, herbicidal activities and severity of crop injury were evaluated on a scale of zero to five by the Following criteria:

| Score | Herbicidal activity | | Crop injury |
|---|---|---|---|
| 5 | 100% control | (0% weed) | withered and died |
| 4 | 80% control | (20% weed) | severe injury |
| 3 | 0% control | (40% weed) | medium injury |
| 2 | 40% control | (60% weed) | slight injury |
| 1 | 20% control | (40% weed) | very sliht injury |
| 0 | 0% control | (100% weed) | no injury |

For comparison, the following control compounds were used:

Comparison I (see Japanese Laid-open Patent Publication Nos. 1-121279 and 2-1481 )

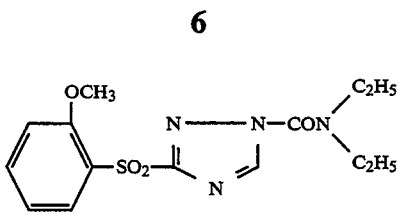

Comparison II (see Japanese Laid-open Patent Publication No. 2-1481)

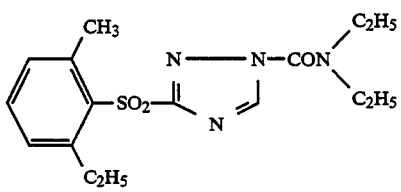

Comparison III (see Japanese Laid-open Patent Publication No. 2-1481)

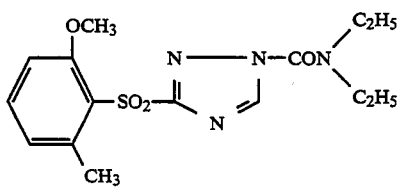

Comparison IV (newly synthesized by the present inventors by referring to Japanese Laid-open Patent Publication Nos. 1-121279 and 2-1481)

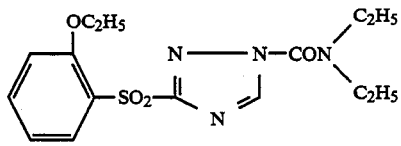

m.p. 81°-82 ° C.

TABLE 2

| Compound No. | Dose (g/a) | Digitaria ciliaris | Chenopodium album | Echinochloa crusgalli | Crop injury (wheat) | Crop injury (soybean) |
|---|---|---|---|---|---|---|
| 1 | 0.25 | 3.5 | 0 | 0 | 0 | 0 |
|  | 0.5 | 5 | 0 | 0 | 0 | 0 |
|  | 1 | 5 | 4 | 4 | 0 | 0 |
|  | 3 | 5 | 5 | 5 | 0 | 0 |
| 2 | 0.25 | 3 | 0 | 0 | 0 | 0 |
|  | 0.5 | 5 | 0 | 0 | 0 | 0 |
|  | 1 | 5 | 2 | 3 | 0 | 0 |
|  | 3 | 5 | 5 | 5 | 0 | 0 |
| Comparison 1 | 0.25 | 0 | 0 | 0 | 0 | 0 |
|  | 0.5 | 2 | 0 | 0 | 0 | 0 |
|  | 1 | 3 | 1 | 1 | 0 | 0 |
|  | 3 | 5 | 1 | 2 | 0 | 0 |
| Comparison 2 | 0.25 | 0 | 0 | 0 | 0 | 0 |
|  | 0.5 | 2.5 | 0 | 0 | 0 | 0 |
|  | 1 | 3.5 | 1 | 1 | 0 | 0 |
|  | 3 | 5 | 1 | 2 | 0 | 0 |
| Comparison 3 | 0.25 | 0 | 0 | 0 | 0 | 0 |
|  | 0.5 | 2 | 0 | 0 | 0 | 0 |
|  | 1 | 3 | 1 | 1 | 0 | 0 |
|  | 3 | 5 | 2 | 3 | 0 | 0 |

TABLE 2-continued

| Compound No. | Dose (g/a) | Digitaria ciliaris | Chenopodium album | Echinochloa crusgalli | Crop injury (wheat) | Crop injury (soybean) |
| --- | --- | --- | --- | --- | --- | --- |
| Comparison 4 | 0.25 | 0 | 0 | 0 | 0 | 0 |
| | 0.5 | 0 | 0 | 0 | 0 | 0 |
| | 1 | 2 | 0 | 0 | 0 | 0 |
| | 3 | 4 | 0 | 1 | 0 | 0 |

TABLE 3

| Compound No. | Dose exhibiting 90% herbicidal activity (g/a) | Ratio Compound No. 1 | Ratio Compound No. 2 |
| --- | --- | --- | --- |
| 1 | 0.35 | 1 | — |
| 2 | 0.38 | — | 1 |
| Comparison 1 | 2.1 | 6 | 5.5 |
| Comparison 2 | 1.9 | 5.4 | 5 |
| Comparison 3 | 2.1 | 6 | 5.5 |
| Comparison 4 | >3 | >8.5 | >7.8 |

The data in Tables 2 and 3 clearly demonstrate that the compounds of the present invention exhibit excellent herbicidal activities in lower doses than the comparison compounds.

The following are several examples of formulations of the herbicide of the present invention.

| Formulation Example 1 (Granule) | |
| --- | --- |
| Compound No. 4 | 0.8 (parts by weight) |
| Sodium lignin sulfonate | 2 |
| Bentonite | 30 |
| Talc | 66.5 |

These components were intimately mixed to obtain a homogeneous composition, which was granulated to form granules.

| Formulation Example 2 (Wettable powder) | |
| --- | --- |
| Compound No. 2 | 0 (parts by weight) |
| Sodium alkylsulfate | 2.5 |
| Polyoxyethylene alkylphenylether | 2.5 |
| Clay | 45 |

These components were intimately mixed to obtain a homogeneous composition, which was finely ground to form a wettable powder.

| Formulation Example 3 (Emulsifiable concentrate) | |
| --- | --- |
| Compound No. 1 | 20 (parts by weight) |
| Alkylbenzenesulfonate salt | 3 |
| Polyoxyethylene alkylarylether | 10 |
| Xylol | 67 |

These components were intimately mixed to obtain a@ homogeneous emulsifiable concentrate.

We claim:

1. A triazole compound represented by the formula:

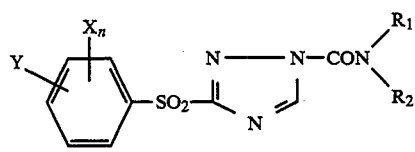

wherein X denotes a hydrogen atom, a halogen or a lower alkyl group, Y denotes a halogen substituted lower alkoxy group, $R_1$ and $R_2$ which may be the same or different each denotes an ethyl or propyl group, and n is an integer of 0-4.

2. A triazole compound as claimed in claim 1 which is represented by the formula:

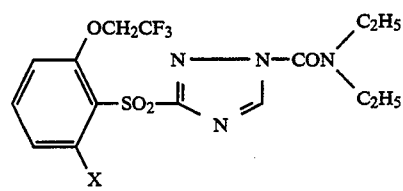

wherein X denotes a hydrogen atom, a halogen or a lower alkyl group.

3. A herbicidal composition comprising a carrier and as an active ingredient an herbicidally effective amount of a triazole compound represented by the formula:

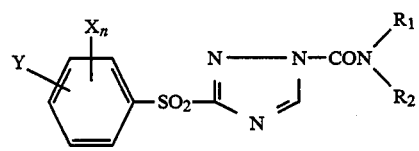

wherein X denotes a hydrogen atom, a halogen or a lower alkyl group, Y denotes a halogen substituted lower alkoxy group, $R_1$ and $R_2$ which may be the same or different each denotes an ethyl or propyl group, and n is an integer of 0-4.

4. A herbicidal composition comprising a carrier and as an active ingredient an herbicidally effective amount of a triazole compound of the formula:

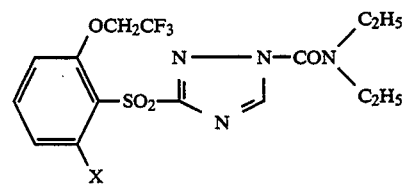

wherein X denotes a hydrogen atom, a halogen or a lower alkyl group.

5. A composition according to claim 3, wherein said triazole compound is present in said composition in an amount of 0.05-95 wt%.

6. A composition according to claim 4, wherein said triazole compound is present in said composition in an amount of 0.05 wt %.

* * * * *